(12) United States Patent
Faustmann et al.

(10) Patent No.: US 9,689,846 B2
(45) Date of Patent: Jun. 27, 2017

(54) DEVICE AND METHOD FOR DETERMINING PROPERTIES OF A MEDIUM

(75) Inventors: Hendrik Faustmann, Coburg (DE); Michael Münch, Coburg (DE)

(73) Assignee: SENSACTION AG, Coburg (DE)

(*) Notice: Subject to any disclaimer, the term of this patent is extended or adjusted under 35 U.S.C. 154(b) by 645 days.

(21) Appl. No.: 14/118,532

(22) PCT Filed: May 18, 2012

(86) PCT No.: PCT/EP2012/059289
§ 371 (c)(1),
(2), (4) Date: Dec. 10, 2013

(87) PCT Pub. No.: WO2012/156517
PCT Pub. Date: Nov. 22, 2012

(65) Prior Publication Data
US 2014/0083194 A1    Mar. 27, 2014

(30) Foreign Application Priority Data
May 19, 2011   (DE) .................. 10 2011 076 132

(51) Int. Cl.
*G01N 29/02*  (2006.01)
*G01N 29/24*  (2006.01)
(Continued)

(52) U.S. Cl.
CPC .......... *G01N 29/32* (2013.01); *G01N 29/022* (2013.01); *G01N 29/032* (2013.01);
(Continued)

(58) Field of Classification Search
CPC .............. G01N 29/022; G01N 29/032; G01N 29/2462; G01N 29/32; G01N 2291/02818;
(Continued)

(56) References Cited

U.S. PATENT DOCUMENTS 4,350,916 A  *  9/1982  August .................... H03H 3/08
                                                        310/313 B
4,691,714 A     9/1987  Wong et al.
(Continued)

FOREIGN PATENT DOCUMENTS

CN    1229469 A    9/1999
CN    1632546 A    6/2005
(Continued)

OTHER PUBLICATIONS

CN Office Action dated Feb. 4, 2015 as received in Application No. 201280024286.6 (English Translation).
(Continued)

*Primary Examiner* — J M Saint Surin
(74) *Attorney, Agent, or Firm* — Maschoff Brennan

(57) ABSTRACT

A device for determining properties of a medium, comprising a carrier which can be brought in contact with the medium; at least one transmitter arranged on the carrier for exciting acoustic waves in the carrier; at least one receiver arranged on the carrier for receiving acoustic waves which originate from waves excited in the carrier by means of the transmitter; and first and second material regions arranged on the carrier, wherein the second material region absorbs sound waves with the frequency of the acoustic waves excited in the carrier more strongly than the first material region. The carrier has a first surface with which it is to be brought in con-tact with the medium and a second surface which faces away from the first surface, wherein the transmitter as well as the first and the second material region are arranged on the second surface.

15 Claims, 1 Drawing Sheet

(51) Int. Cl.
*G01N 29/032* (2006.01)
*G01N 29/32* (2006.01)

(52) U.S. Cl.
CPC .......... *G01N 29/2462* (2013.01); *G01N 2291/02818* (2013.01); *G01N 2291/02881* (2013.01); *G01N 2291/0423* (2013.01); *G01N 2291/0427* (2013.01)

(58) Field of Classification Search
CPC . G01N 2291/02881; G01N 2291/0423; G01N 2291/0427
USPC .......................................................... 73/629
See application file for complete search history.

(56) References Cited

U.S. PATENT DOCUMENTS

| | | | |
|---|---|---|---|
| 5,521,565 A * | 5/1996 | Anemogiannis | H03H 9/6489 310/313 B |
| 5,936,150 A | 8/1999 | Kobrin et al. | |
| 6,216,544 B1 | 4/2001 | Adachi et al. | |
| 6,513,365 B1 | 2/2003 | Bruetting et al. | |
| 6,763,698 B2 * | 7/2004 | Greenwood | G01N 9/002 73/30.01 |
| 7,656,070 B2 | 2/2010 | Kadota et al. | |
| 8,661,904 B2 * | 3/2014 | Schmitt | 73/290 V |
| 9,074,981 B2 * | 7/2015 | Reichel | G01N 11/16 |
| 9,121,816 B2 * | 9/2015 | Faustmann | G01N 29/032 |
| 2005/0223808 A1 * | 10/2005 | Myers | G01N 29/024 73/629 |
| 2009/0114798 A1 | 5/2009 | Tigli et al. | |
| 2012/0060591 A1 | 3/2012 | Faustmann et al. | |

FOREIGN PATENT DOCUMENTS

| | | | |
|---|---|---|---|
| CN | 101034083 A | 9/2007 | |
| CN | 101133321 A | 2/2008 | |
| DE | 10 2009 048 646 A1 | 3/2011 | |
| WO | 2008/034878 A2 | 3/2008 | |
| WO | WO2010034715 * | 4/2010 | .......... G01B 17/025 |
| WO | 2010/118793 A1 | 10/2010 | |
| WO | WO2010118793 * | 10/2010 | .......... G01N 29/032 |
| WO | 2010/136350 A1 | 12/2010 | |

OTHER PUBLICATIONS

Josse., et al., "Guided Shear Horizontal Surface Acoustic Wave Sensors for Chemical and Biochemical Detection in Liquids," Analytical Chemistry, vol. 73, Issue 24, Dec. 15, 2001, pp. 5937-5944.
Mingxi., "Detection of Acoustic Bulk Waves by Interdigital Transducer at an Interface of Piezoelectric Crystal and Liquid," Piezoelectrics & Acoustooptics, vol. 21, Issue 5, May 21, 1999, pp. 1-12.
Vellekoop, J. V., "Acoustic wave sensors and their technology", Ultrasonics, vol. 36, Issue 1-5, Feb. 1998, pp. 7-14.
Xia., et al., "A New Type of Liquid Density Sensor Using IDT Technics," Piezoelectrics &. Acoustooptics, vol. 27, Issue 6, Dec. 2005, pp. 602-605.

\* cited by examiner

DEVICE AND METHOD FOR DETERMINING PROPERTIES OF A MEDIUM

CROSS-REFERENCE TO A RELATED APPLICATIONS

This application is a National Phase Patent Application of International Patent Application Number PCT/EP2012/059289, filed on May 18, 2012, which claims priority of German Patent Application Number 10 2011 076 132.2, filed on May 19, 2011.

BACKGROUND

This invention relates to a device for determining properties of a medium and to a method for manufacturing such a device.

The use of sound waves for determining properties (e.g the temperature or the composition) of a liquid or gaseous medium is known from the prior art. For example, WO 2008/034878 discloses a device for exciting surface sound waves in a carrier adjacent to the medium to be examined, wherein by means of the surface sound waves physical and/or chemical properties of the medium are determined.

SUMMARY

A problem underlying the invention consists in indicating a device for determining properties of a medium, which provides for a rather efficient examination of the medium. Furthermore, a method for manufacturing such a device should be indicated.

According to an exemplary embodiment of the invention, there is provided a device for determining properties of a medium, comprising
- a carrier which can be brought in contact with the medium;
- at least one transmitter arranged on the carrier for exciting acoustic waves in the carrier;
- at least one receiver arranged on the carrier for receiving acoustic waves which originate from acoustic waves excited in the carrier by means of the transmitter; and
- a first material region arranged on the carrier; and
- a second material region arranged on the carrier, wherein the second material region is of such a kind that it absorbs sound waves with the frequency of the acoustic waves excited in the carrier more strongly than the first material region.

The first and the second material region in particular ensure that a propagation of the sound waves in an undesired direction and hence e.g. reflections on other structures of the device and thus echoes in the receiver signal are suppressed or at least reduced. In addition, external disturbances can be attenuated, the signal-to-noise ratio of the receiver signal can be increased and/or the dependence of the receiver signal on properties of the medium can be linearized. In addition, the first and the second material region can mechanically stabilize the device and e.g. also counteract fogging on the carrier and/or the transmitter or the receiver.

The transmitter in particular is formed such that it excites acoustic surface waves e.g. in the form of Lamb waves or in the form of a mixed form of Lamb and Rayleigh waves in the carrier. For example, acoustic surface wave pulses generated in the carrier. The acoustic surface waves excited in the carrier in part couple out from the carrier into the medium, i.e. there is effected an at least partial conversion of the acoustic surface waves running in the carrier into volumetric sound waves in the medium. Conversely, the volumetric sound waves excited in the medium in part are converted back into surface sound waves in the carrier, which then can be registered with the receiver. A part of the acoustic surface waves excited in the carrier, however, also will directly run in the carrier to the receiver and will be detected there. It is, however, also conceivable that surface waves are not or at least not exclusively excited in the carrier by means of the transmitter, but in general sound waves, which e.g. have a longitudinal component (along the carrier) and a transversal component (vertically to the carrier). It is also possible that purely longitudinal waves are excited in the carrier.

In addition, at least one of the two material regions can be of such a kind that a conversion of sound waves excited in the carrier into volumetric sound waves in the medium is promoted, i.e. a larger part of the sound waves in the carrier couples out into the medium than would be the case without the material regions. In particular, the material regions are formed such that on the one hand the first material region promotes the coupling in of sound waves from the carrier into the medium and on the other hand coupling out from the carrier in a direction away from the medium is attenuated by the second material region absorbing more strongly.

In addition, in particular the first material region can be formed such that it promotes the excitation of a certain type of sound waves, i.e. sound waves with a particular longitudinal and transversal component. For example, the first material region and/or the second material region is formed such that surface waves or creeping waves preferably are excited in the carrier. It is also conceivable that the first and/or the second material region is formed such that in the carrier a first wave type (e.g. surface waves) is excited at a first frequency (or a first frequency range) and a second wave type (e.g. creeping waves) is excited at a second frequency (or a second frequency range).

According to an exemplary development of the invention, the first material region also is of such a kind that it reflects sound waves with the frequency of the waves excited in the carrier more strongly than the second material region. In particular, the more reflective first material region at least sectionally is arranged between the carrier and the second material region, wherein the two material regions in particular are arranged on a side of the carrier which in operation of the device faces away from the medium to be examined. Thus, in particular the more reflective first material region counteracts an exiting of acoustic waves from the carrier via a surface of the carrier facing away from the medium, and in particular promotes, as mentioned above, the overcoupling of waves into the medium, i.e. the conversion of acoustic waves excited in the carrier into volumetric sound waves in the medium, more strongly than the second material region.

It is possible that in a first frequency range the first material region reflects sound waves more strongly than in a second frequency range, so that in the first frequency range a larger part of the sound waves excited in the carrier will couple over into the medium than in the second frequency range, i.e. the conversion of sound waves in the carrier into volumetric sound waves is effected in a frequency-dependent manner or the frequency dependence of the conversion is changed (e.g. amplified), as already mentioned above. Due to the frequency dependence of the reflection behavior of the first material region, there can also be effected a frequency-dependent excitation of a certain wave type in the carrier, as also already mentioned above.

The properties of the acoustic waves detected by the receiver, i.e. on the one hand surface sound waves resulting from the re-conversion of volumetric sound waves, or on the other hand surface sound waves which are running directly in the carrier from the transmitter to the receiver, depend on properties of the medium (for example its composition, mass density and/or temperature). Correspondingly, the (electric) receiver signal also depends on the properties of the medium, so that by analysis of the receiver signal properties of the medium can be determined. In particular, the running time and the amplitude of the surface sound waves arriving at the receiver (and hence the time behavior and the amplitude of the receiver signal) depend on properties of the medium.

The device according to the invention thus represents a sensor which can be used in particular for determining properties of a medium in the form of a liquid and/or of a soft material (for example a biological tissue or a gel). It is, however, also conceivable that the device is used for determining properties of a medium in the form of a gas. For example, the device is partly or completely immersed into the medium or connected with a reservoir filled with the medium or with a line traversed by the medium such that the medium can flow through the device. With the device according to the invention properties of the medium can be tracked continuously, in order to determine time-dependent properties ("monitoring") In addition, a locally resolved measurement of a spatially inhomogeneously distributed property of the medium is possible.

The carrier of the device in particular has a first surface with which it is to be brought in contact with the medium and a second surface which faces away from the first surface, wherein for example the transmitter as well as the first and the second material region are arranged on the second surface. It is, however, also possible that the transmitter is located on the first surface and also at least a partial region of the first and/or the second material region likewise is arranged on the first surface.

The carrier for example is a substantially planar (plate-like), in particular at least substantially rigid, structure, wherein the carrier also can be formed of a plurality of partial elements, for example a plurality of plates spaced from each other. The carrier can of course also be formed in one piece.

In addition it is conceivable that the carrier is a spatial structure, for example a hollow cylinder. When the carrier is designed as hollow cylinder, the carrier forms a shell surface which defines an inner volume to be filled with the medium to be examined.

Furthermore, a portion of the carrier adjacent to the medium itself can include a cavity in which the transmitter and/or the receiver are located. For example, when the carrier is formed as hollow cylinder, the wall of the hollow cylinder or, in the case of a plate as carrier, the plate can include the cavity. For example, the cavity formed by a portion of the carrier is defined by an inner wall which in operation of the device is in physical contact with the medium with an inner side, and by an outer wall which forms an outside of the device. In addition, it is conceivable that the first and/or the second material region likewise are arranged in this cavity.

According to another exemplary aspect of the invention, the first material region includes a first material and the second material region includes a second material, wherein the second material has a greater mass density than the first material. Furthermore it is conceivable that the second material region has a higher acoustic impedance than the first material region, wherein "acoustic impedance" in particular is understood to be the quotient of sound pressure and sound flux.

The first and the second material region include at least one material which is in its solid state, i.e. the first and the second material region are not exclusively formed by a gas (air).

A material useful for the first material region for example is a foam-like material (for example polyurethane foam). As material for the second material region, e.g. silicone or epoxy resin is used. The material of the first material region and/or the material of the second material region can include a fill, e.g. air bubbles and/or metal particles. For example, the properties of the first and/or the second material region selectively are adapted via the kind (e.g. the size of the metal particles) and/or the concentration of the fill. Thus, it is possible that depending on the kind and/or concentration of the fill the first and/or the second material region promotes the conversion of sound waves excited in the carrier into volumetric sound waves in the medium more strongly in a first frequency range (e.g. reflects sound waves more strongly in this frequency range) than in a second frequency range; e.g. the conversion is suppressed in the second frequency range. It is also conceivable that in dependence on the kind and/or the concentration of the fill in the carrier a certain wave type is excited preferably.

It is also conceivable that the first material region includes a paint or a metallic coating, which for example at the same time can be used as conductor path for contacting components (for example of the transmitter and/or the receiver).

In a second aspect, the invention according to an exemplary embodiment relates to a device for determining properties of a medium, comprising a carrier which can be brought in contact with the medium;

at least one transmitter arranged on the carrier for exciting acoustic waves, in particular surface waves, in the carrier;

at least one receiver arranged on the carrier for receiving acoustic waves which originate from acoustic waves excited in the carrier by means of the transmitter;

a material region arranged on the carrier which is of such a kind that it effects a guidance of the acoustic waves excited in the carrier and/or a conversion of acoustic waves in the carrier into volumetric sound waves in the medium or influences a conversion of volumetric sound waves in the medium into acoustic waves in the carrier in a locally dependent manner.

In particular, the material region consists of the above-explained first and second material region or it includes such material regions. In other words, the material region comprises a first material region which absorbs sound waves with the frequency of the waves excited in the carrier more strongly than the second material region, wherein the first material region also can be formed such that it reflects sound waves with the frequency of the waves excited in the carrier more strongly than the second material region. In particular, the first material region can be formed such that it promotes the excitation of a certain wave type and/or the conversion of the waves excited in the carrier into volumetric sound waves in the medium (e.g. locally dependent), as described above.

The material region in particular is structured such that together with the carrier it defines a waveguide which guides the acoustic waves. For example, the material region extends along a (for example straight) line in a strip-like manner, which line defines a path for the propagation of the surface sound waves excited in the carrier. It is also conceivable that the conversion of waves in the carrier into volumetric sound waves or vice versa of volumetric sound waves in the medium into acoustic waves in the carrier is selectively, i.e. in particular in a locally dependent manner or in dependence on the mode or the type of the acoustic waves, influenced by the material region. For example, at certain points of the carrier the material region prevents a coupling out of sound waves into the medium or vice versa a coupling out of sound waves from the medium into the carrier. In particular, applying a material region which is structured for guiding the waves can replace a structuring of the carrier. Structuring of the carrier, in order to realize a selective guidance of the waves, nevertheless is possible, but in particular when using a carrier of a non-piezoelectric material mostly is expensive.

The material region in particular is arranged on a surface of the carrier which in operation of the device faces away from the medium. However, it is also conceivable that at least a part of the material region, as already mentioned above in connection with the first aspect of the invention, is arranged on an inside, i.e. on a side of the carrier facing the medium.

In a third aspect, the invention according to a further exemplary embodiment relates to a device for determining properties of a medium, comprising
  a carrier which can be brought in contact with the medium;
  at least one transmitter arranged on the carrier for exciting acoustic waves, in particular surface waves, in the carrier;
  at least one receiver arranged on the carrier for receiving acoustic waves which originate from waves excited in the carrier by means of the transmitter;
  at least one material region arranged on the carrier, which is arranged on a surface of the carrier which in operation of the device faces the medium, wherein the material region has an acoustic impedance which lies between the acoustic impedance of the medium and that of the carrier.

In particular, the acoustic impedance of the material region is greater than the acoustic impedance of the medium and smaller than the acoustic impedance of the carrier. However, the reverse case also is conceivable, e.g. with a highly viscous liquid as medium.

By means of the material region arranged on an inside of the carrier, an impedance adaptation thus is effected between the carrier (in particular formed of a non-piezoelectric material) and the medium to be examined. As material for the (impedance adaptation) material region, a plastic material (in particular Teflon) can be used, for example. It is also possible that the material region comprises an oxide layer, which is produced e.g. by anodizing. It is also conceivable that instead of or in addition to an oxide layer another layer with passivation properties (e.g. a nitride layer) or a nanocoating is used. Of course, there can also be arranged a plurality of material layers with different acoustic impedances (increasing towards the carrier).

The impedance adaptation by means of the material region in particular results in a better efficiency of the coupling out of energy from the carrier into the medium and thus in greater amplitudes of the receiver signal and/or an improved signal-to-noise ratio. It would also be conceivable that via the impedance-adapting material region different sound energies are coupled in from the carrier into the medium in a locally dependent manner, in order to perform a selective (locally dependent) examination of the medium.

In particular, the material region therefore is not formed continuously, but is divided into a plurality of segments spaced from each other.

In addition, the material region changes the mechanical properties of the inner surface of the carrier, for example the roughness, the hardness, the chemical resistance and/or adhesion properties of the inner surface, which likewise can be utilized for influencing the propagation of the waves.

In particular, the impedance-adapting material region is formed in the form of a coating on the inside of the carrier, wherein the coating e.g. can also be structured, in order to produce or amplify a guidance of the acoustic waves excited in the carrier. For example, the structured coating on the inside of the carrier cooperates with a first and second material region structured as described above on the side (surface) of the carrier facing away from the medium, in order to realize an improved guidance of the surface sound waves in the carrier.

In a fourth aspect, the invention according to an exemplary embodiment relates to a device for determining properties of a medium, which in particular is formed as described above, comprising
  a carrier which can be brought in contact with the medium;
  at least one transmitter arranged on the carrier for exciting acoustic waves in the carrier;
  at least one receiver arranged on the carrier for receiving acoustic waves which originate from waves excited in the carrier by means of the transmitter;
  a material region which at least partly extends around the transmitter and/or the receiver.

In particular, the transmitter is an interdigital transducer, wherein the material region is designed such that the resonance amplitude of the interdigital transducer is influenced by the material region. For example, the material region is formed such that the interdigital transducer excites acoustic surface waves in the carrier, wherein in the carrier it only excites the asymmetric fundamental mode of the acoustic sound waves (and not the symmetric fundamental mode) or vice versa only the symmetric fundamental mode, but not the asymmetric fundamental mode. Analogously, a desired wave mode selectively can be detected via a corresponding configuration of the material region surrounding the receiver.

In other words, via the material region surrounding the transmitter a certain acoustic mode (or a certain wave type) selectively can be excited in the carrier, wherein in particular the symmetric and the asymmetric mode have different propagation velocities and also can interact differently with the medium. For example, the interaction of the asymmetric fundamental mode in the carrier in particular depends on the temperature and the composition (e.g. the concentration of a substance of a substance mixture) of the medium, so that when only the asymmetric fundamental mode is excited, an examination especially of these properties is possible. In addition, when only the asymmetric fundamental mode is excited, accretions, coatings or encrustations on the inside of the carrier in particular become noticeable in the receiver signal. The interaction of the symmetric fundamental mode with the medium, on the other hand, largely is dependent on the temperature and the thickness of the carrier.

It is also conceivable that the material region is designed such that the conversion of waves excited in the carrier into volumetric sound waves in the medium is influenced selectively and/or preferably a certain wave type in the carrier is excited, as explained above.

In addition, an increased protection of the transmitter and/or the receiver can be realized via the material region which extends around the transmitter and/or the receiver. In particular, the material region can protect the transmitter and/or the receiver against mechanical and/or thermal loads (e.g. in use of the device according to the invention during a welding process) or against air humidity. For example, electric connecting lines to the transmitter or to the receiver are protected, so that they cannot tear off in particular also due to a force acting on the device (e.g. vibration).

It should be noted that the material region can of course also consist of different regions, e.g. also regions spaced from each other, wherein e.g. a first material region surrounds the transmitter and a second, separate material region surrounds the receiver. It is, however, also conceivable that a continuous material region extends both around the transmitter and around the receiver.

The invention also relates to a method for manufacturing a device according to any of the preceding claims, with the following steps:
  providing a carrier;
  arranging a transmitter on the carrier for generating acoustic waves in the carrier;
  arranging a receiver on the carrier for receiving acoustic waves propagating in the carrier;
  arranging a first and a second material region on the carrier, wherein the second material region absorbs sound waves with the frequency of the acoustic waves excited in the carrier more strongly than the first material region, and/or
  arranging a material region on the carrier which is of such a kind that it effects a guidance of the waves excited in the carrier and/or a conversion of acoustic waves in the carrier into volumetric sound waves in the medium or influences a conversion of volumetric sound waves in the medium into acoustic waves in the carrier in a locally dependent manner, and/or
  arranging a material region on a surface of the carrier, which in operation of the device faces the medium, wherein the material region has an acoustic impedance which lies between the acoustic impedance of the medium and the acoustic impedance of the carrier, and/or
  arranging a material region which at least partly extends around the transmitter and/or the receiver.

BRIEF DESCRIPTION OF THE DRAWINGS

The invention will subsequently be explained in detail by means of exemplary embodiments with reference to the Figures.

DETAILED DESCRIPTION

Figure 1:
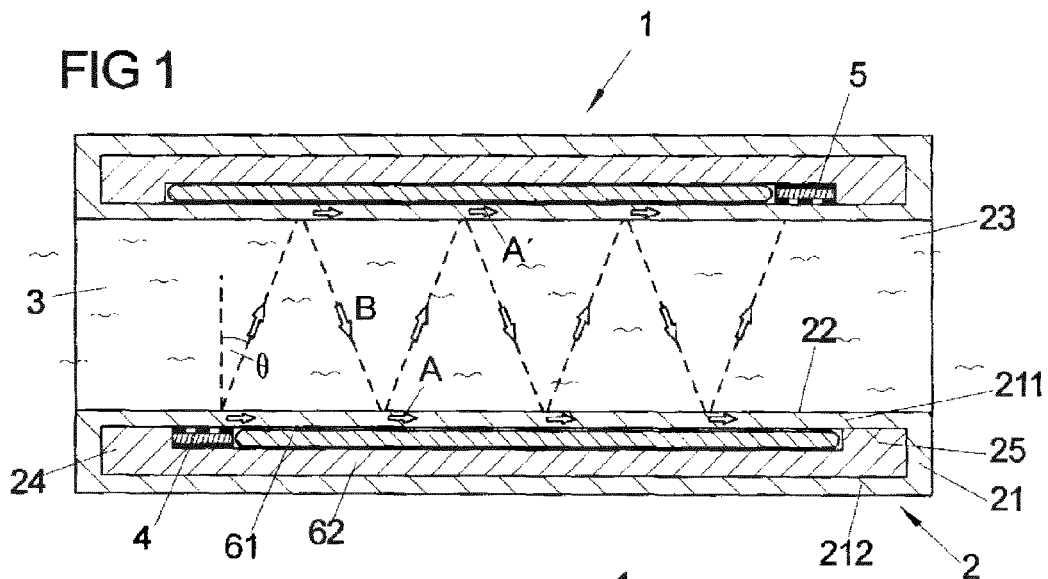
FIG. 1 shows a sectional view of a device for determining properties of a medium according to a first exemplary embodiment of the invention.

The device 1 according to the invention as shown in FIG. 1 includes a carrier in the form of a hollow cylinder 2, wherein an inner surface 22 of a shell 21 of the hollow cylinder 2 defines an inner volume 23 of the device 1. In the inner volume 23 a medium in the form of a liquid 3 is present, wherein chemical and/or physical properties of the liquid 3 can be determined by means of the device 1 according to the invention. The hollow cylinder 2 in particular is formed of a non-piezoelectric material (e.g. a metal or a plastic material).

The shell 21 of the hollow cylinder 2 at least sectionally is formed as hollow body, wherein a first (inner) portion 211 of the shell 21, which forms the above-mentioned inner surface 22, defines the cavity 24 towards the inner volume 23 and a second (outer) portion 212 defines the cavity 24 to the outside.

On a surface 25 of the first portion 211 facing the cavity 24 a transmitter 4 is arranged for exciting acoustic surface waves (arrows A) in the carrier, i.e. in the first portion 211 of the shell 21.

A part of the surface sound waves A excited in the portion 211 will couple out into the liquid 3, i.e. is converted into volumetric sound waves B in the liquid. A part of these volumetric sound waves B in turn is reflected on another region of the inner portion 211, e.g. on a region opposed to the transmitter 4 in a direction vertical to the propagation direction A of the surface waves (i.e. radially), and another part is converted back into acoustic surface sound waves A' in the carrier. These surface sound waves A' are detected by a receiver 5, wherein the receiver 5 likewise is arranged on a side of the inner portion 211 facing away from the cavity 24.

However, the receiver 5 is arranged on a region of the inner portion 211, which is radially opposed to the region of the inner portion 211 with the transmitter 4. It is, however, also conceivable that the receiver 5 is placed at some other point, e.g. such that it lies on a straight line in common with the transmitter 4, which extends along the longitudinal axis of the hollow cylinder 2. In addition, it is conceivable that at least one further receiver is provided, which is arranged e.g. on the same region of the inner portion 211 as the transmitter 4, e.g. at least approximately lies on a straight line in common with the transmitter 4 along the longitudinal axis of the hollow cylinder 2.

A part of the surface sound waves excited by the transmitter 4 in the inner portion 211 also will reach the receiver 5 directly, i.e. via the inner portion 211 of the hollow cylinder 2, so that the signal generated by the receiver contains both a component which originates from the surface sound waves A' obtained by mode reconversion, and a component which is produced upon receipt of surface sound waves which are running directly from the transmitter 4 to the receiver 5. Both components of the receiver signal are dependent on properties of the liquid 3, so that by evaluating the signal components properties of the liquid can be inferred.

In the cavity 24 of the shell 21 a first and a second material region are present in the form of a first encapsulation 61 and a second encapsulation 62. The first encapsulation 61 is arranged directly on the surface 25 of the first portion 211 of the shell 21, while the second encapsulation 62 only sectionally is in contact with the first portion 211. Otherwise, the second encapsulation 62 extends between the first encapsulation 61 and the outer portion 212 of the shell 21, wherein it surrounds both the transmitter 4 and the receiver 5 on a backside facing away from the first portion 211 of the hollow cylinder 2 and laterally on a side facing away from the first encapsulation 61. The second encapsulation 62 consists of a material which absorbs sound waves with a frequency of the excited surface sound waves A more strongly than the first encapsulation 61. At the same time, the material of the first encapsulation 61 reflects the surface sound waves A more strongly than the material of the second encapsulation 62.

The first and the second encapsulation 61, 62 thus in particular prevent an undesired coupling out of the surface sound waves A away from the liquid 3 (i.e. into the cavity 24) or at least attenuate surface sound waves extending along an undesired propagation path in the hollow cylinder 2. In addition, by means of the first and the second encapsulation a reproducible state of the backside (i.e. the outer surface 25) is realized, which is rather independent of external influences (i.e. the surroundings of the device 1).

In addition, in particular the first encapsulation 61 can be designed such that it influences the conversion of acoustic waves excited in the hollow cylinder 2 (e.g. locally dependent), as explained above. It is also possible that the first encapsulation 61 is formed such that in the hollow cylinder 2 preferably (e.g. exclusively) a particular wave type (e.g. said surface waves) is excited. In particular, the first encapsulation is designed such (by the choice of the material and/or its dimensions) that the type of the excited waves depends on the excitation frequency of the transmitter. For example, the first encapsulation 61 promotes the excitation of a first wave type (e.g. surface waves) in a first frequency range and the excitation of a second wave type (e.g. creeping waves, which chiefly or exclusively propagate in the wall of the hollow cylinder 2) in a second frequency range. The fact that a wave type is "promoted" in particular means that the effective sound refraction index of the hollow cylinder 2 is changed by the first encapsulation 61 such that the desired wave type can propagate in the hollow cylinder exclusively or for the most part.

Thus, it is possible for example to switch over from a normal operation (first frequency range with excitation e.g. of surface waves) to a self-test operation (second frequency range with excitation e.g. of creeping waves), wherein the creeping waves excited in the second frequency range only are running in the hollow cylinder from the transmitter to the receiver, so that e.g. a damage of the hollow cylinder is detectable.

In addition, the first and the second encapsulation 61, 62 can be structured (e.g. formed strip-like), in order to impart a desired propagation direction to the surface sound waves A. In the exemplary embodiment of FIG. 1, the second encapsulation 62 has a greater thickness (vertically to the first portion 211 of the carrier 2) than the first encapsulation 61. This is, however, not absolutely necessary, and it is also possible that the first encapsulation has a greater thickness than the second encapsulation or the encapsulations approximately have the same thickness.

Furthermore, the encapsulations 61, 62 each can be formed continuously, i.e. extend continuously from the region of the first portion 211 of the hollow cylinder 2, on which the transmitter 4 is arranged, up to the region of the first portion 211 of the hollow cylinder 2 with the receiver 5. In particular, the first and the second encapsulation 61, 62 extend along the complete inner circumference of the first portion 211 of the carrier 2. It is, however, also possible that the first and/or the second encapsulation 61, 62 form a plurality of partial regions spaced from each other.

Figure 2:
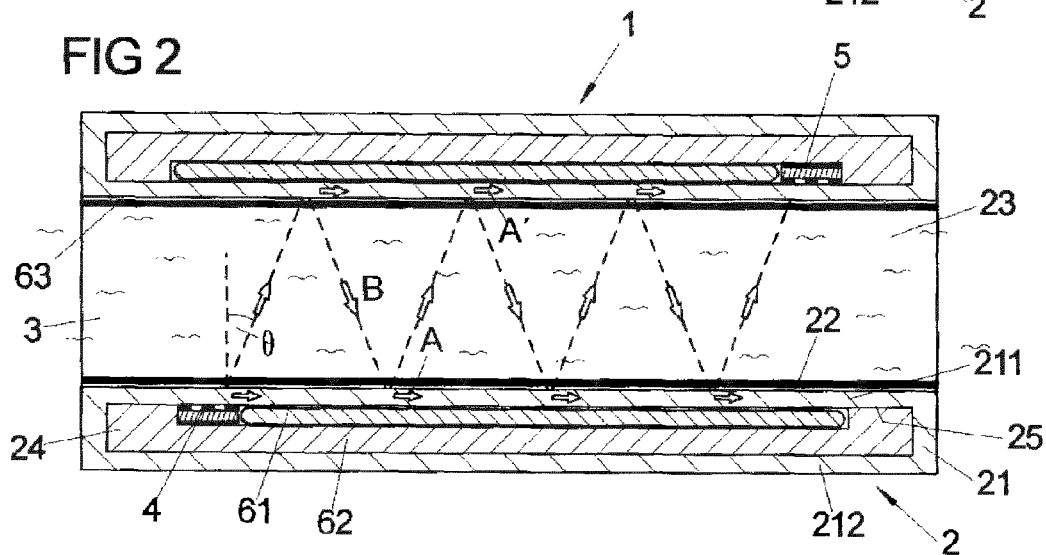
FIG. 2 shows a sectional view of a device according to a second exemplary embodiment of the invention.

FIG. 2 shows a sectional view of a device 1 according to a second exemplary embodiment of the invention. Here, as compared to the exemplary embodiment shown in FIG. 1, a further material region in the form of a coating 63 additionally is arranged on the inside 22 of the inner portion 211 of the shell 21.

The coating 63 has an acoustic impedance which is greater than the acoustic impedance of the liquid 3 to be examined and smaller than the acoustic impedance of the hollow cylinder 2, i.e. of the inner portion 211. Thus, via the coating 63 an adaptation of the impedance of the inner portion 211 to the impedance of the liquid 3 is realized. It is also conceivable that the coating 63 is structured corresponding to the first and the second encapsulation 61, 62, in order to support a guidance of the surface sound waves A. For example, the coating 63 has a plurality of partial regions spaced from each other. It is, however, also possible that the coating 63 is formed continuously and extends e.g. at least with a section along the complete inner circumference of the inner portion 211 of the hollow cylinder 2.

The thickness of the coating 63 in particular is smaller than the thickness of the first portion 211 of the hollow cylinder 2 and in particular smaller than the wavelength of the acoustic surface waves A excited in the first portion 211. As material for the coating there can be used e.g. a material which has a mass density which lies between the mass density of the medium and the material of the carrier. Furthermore, a material might be used in which the sound velocity is greater than the sound velocity in the medium and smaller than in the material of the carrier.

It should be noted that the impedance adaptation by means of the coating 63 can of course also be effected without the first and the second encapsulation 61, 62.

Figure 3:
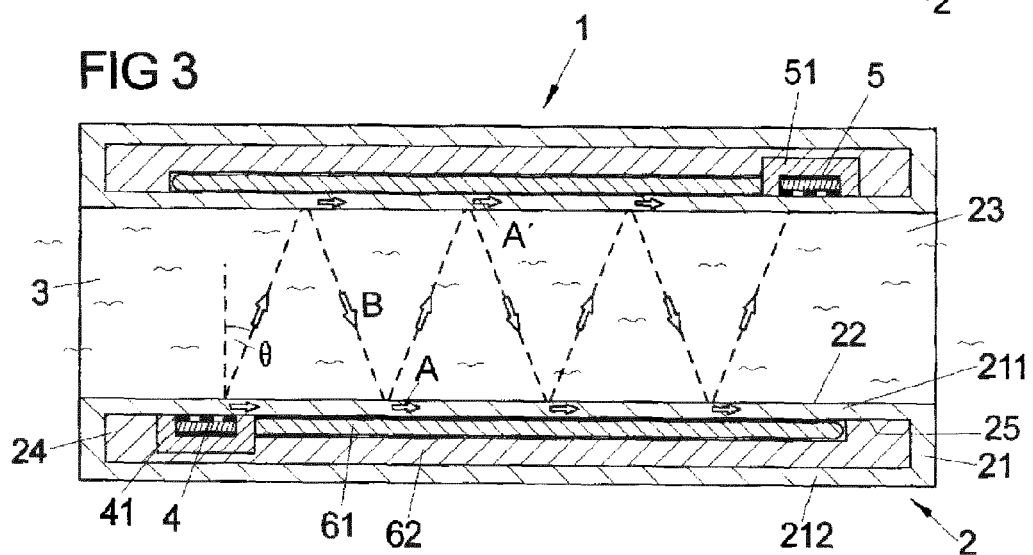
FIG. 3 shows a sectional view of a device according to a third exemplary embodiment of the invention.

FIG. 3 relates to a further exemplary embodiment of the invention. Accordingly, the device 1 according to the invention includes a further material region in the form of a third encapsulation 41 in which the transmitter 4 is embedded, wherein the third encapsulation 41 in particular extends along a side of the transmitter 4 facing away from the inner portion 211 of the hollow cylinder 2.

Furthermore, the material region comprises a fourth encapsulation 51 in which the receiver 5 is embedded, wherein the fourth encapsulation 51 analogous to the third encapsulation 41 extends along a side of the receiver 5 facing away from the inner portion 211 of the hollow cylinder 2.

The third and the fourth encapsulation 41, 51 on the one hand serve the protection of the transmitter and the receiver. Furthermore, the third encapsulation 41 and/or the fourth encapsulation 51 can be formed such that the resonance amplitude of the transmitter 41 formed as interdigital transducer and/or the resonance amplitude of the receiver 5 formed as interdigital transducer are influenced. In particular, the resonance amplitudes can be influenced by the encapsulation 41 or by the encapsulation 51 such that either only the asymmetric fundamental mode is excited (or detected) in the inner portion 211 or only the symmetric fundamental mode. As material for the third and/or fourth encapsulation e.g. an electrically conductive potting material can be used.

The third and the fourth encapsulation 41, 51 in particular are formed by material regions spaced from each other. It is, however, also possible that a continuous encapsulation forms the third and the fourth encapsulation 41, 51. In addition, it is of course also not absolutely necessary that the first and the second encapsulation 6L 62 is arranged in the cavity 24 of the shell 21.

In addition it should be noted that elements of the described exemplary embodiments can of course also be used in combination with each other. It is possible, for example, to additionally provide an inner coating 63 for impedance adaptation also in the exemplary embodiment of FIG. 3.

LIST OF REFERENCE NUMERALS 1 device
2 hollow cylinder 3 liquid
4 transmitter
5 receiver
21 shell
22 inner surface
23 inner volume
24 cavity
25 surface
41 third encapsulation
51 fourth encapsulation
61 first encapsulation
62 second encapsulation
63 coating
211 first portion
212 second portion
A, A' acoustic surface waves
B volumetric sound waves

The invention claimed is:

1. A device for determining properties of a medium, comprising:
   a carrier configured to be brought in contact with the medium;
   at least one transmitter arranged on the carrier for exciting acoustic waves in the carrier;
   at least one receiver arranged on the carrier for receiving acoustic waves which originate from waves excited in the carrier by means of the transmitter;
   a first material region arranged on the carrier; and
   a second material region arranged on the carrier, wherein the second material region is configured to absorb sound waves with the frequency of the acoustic waves excited in the carrier more than the first material region,
   wherein the carrier has a first surface which is configured to be brought in contact with the medium and a second surface which faces away from the first surface, wherein the transmitter as well as the first and the second material region are arranged on the second surface.

2. The device according to claim 1, wherein the first material region is configured to reflect sound waves with the frequency of the waves excited in the carrier more than the second material region.

3. The device according to claim 1, wherein that the first material region at least sectionally extends between the carrier and the second material region.

4. The device according to claim 1, wherein the first material region includes a first material and the second material region includes a second material, wherein the second material has a greater mass density than the first material.

5. The device according to claim 1, further comprising determination means for determining properties of the medium with reference to a signal generated by the receiver upon receipt of acoustic sound waves.

6. A device for determining properties of a medium, comprising:
   a carrier configured to be brought in contact with the medium;
   at least one transmitter arranged on the carrier for exciting acoustic waves in the carrier;
   at least one receiver arranged on the carrier for receiving acoustic waves which originate from acoustic waves excited in the carrier by means of the transmitter; and
   a material region arranged on the carrier which is configured to effect a guidance of the waves (A) excited in the carrier and/or a conversion of acoustic waves (A) in the carrier into volumetric sound waves in the medium or influences a conversion of volumetric sound waves in the medium into acoustic waves in the carrier in a locally dependent manner,
   wherein a first surface of the carrier is configured to be brought into contact with the medium, wherein at least a part of the material region is arranged at a second surface of the carrier facing away from the first surface and thus facing away from the medium during the operation of the device.

7. The device according to claim 6, wherein the material region includes a first and a second material region, wherein the second material region absorbs sound waves with the frequency of the acoustic waves excited in the carrier more than the first material region and/or the first material region reflects sound waves with the frequency of the acoustic waves excited in the carrier more than the second material region.

8. The device according to claim 6, wherein the carrier is to be brought in contact with the medium with a first surface, wherein at least a part of the material region is arranged on a second surface of the carrier, which faces away from the first surface.

9. A device for determining properties of a medium, comprising:
   a carrier configured to be brought in contact with the medium;
   at least one transmitter arranged on the carrier for exciting acoustic waves in the carrier;
   at least one receiver arranged on the carrier for receiving acoustic waves which originate from acoustic waves excited in the carrier by means of the transmitter; and
   at least one material region arranged on the carrier, which is arranged on a surface of the carrier which in operation of the device faces the medium, wherein the material region has an acoustic impedance which lies between the acoustic impedance of the medium and that of the carrier,
   wherein the material region forms a coating on the carrier.

10. The device according to claim 9, wherein the acoustic impedance of the material region is greater than the acoustic impedance of the medium and smaller than the acoustic impedance of the carrier.

11. A device for determining properties of a medium, comprising:
   a carrier configured to be brought in contact with the medium;
   at least one transmitter arranged on the carrier for exciting acoustic waves in the carrier;
   at least one receiver arranged on the carrier for receiving acoustic waves which originate from waves excited in the carrier by means of the transmitter; and
   a material region is formed as an encapsulation embedding the transmitter and/or the receiver,
   wherein the transmitter and/or the receiver is formed in the form of an interdigital transducer, wherein the material region is formed such that the resonance amplitude of the interdigital transducer is influenced by the material region, and
   wherein the material region is formed such that in a first frequency range a first wave type is excited in the carrier and in a second frequency range a second wave type is excited, which is different from the first wave type.

12. The device according to claim 11, wherein in the first frequency range surface waves are excited as first wave type and in the second frequency range longitudinal waves are excited.

13. The device according to claim 11, wherein the material region is formed such that the interdigital transducer excites acoustic surface waves in the carrier, wherein the asymmetric fundamental mode and not the symmetric fundamental mode of the acoustic surface waves is excited.

14. The device according to claim 11, wherein the material region is formed such that the interdigital transducer excites acoustic surface waves in the carrier, wherein the symmetric fundamental mode and not the asymmetric fundamental mode of the acoustic surface waves is excited.

15. A method for manufacturing a device according to claim 1, comprising:
providing a carrier;
arranging a transmitter on the carrier for generating acoustic waves in the carrier;
arranging a receiver on the carrier for receiving acoustic waves propagating in the carrier;
arranging a first and a second material region on the carrier, wherein the second material region absorbs sound waves with the frequency of the acoustic waves excited in the carrier more than the first material region, wherein the carrier has a first surface with which it is to be brought in contact with the medium and a second surface which faces away from the first surface, wherein the transmitter as well as the first and the second material region are arranged on the second surface, and/or
arranging a material region on the carrier which is configured to effect a guidance of the waves excited in the carrier and/or a conversion of acoustic waves in the carrier into volumetric sound waves in the medium or influences a conversion of volumetric sound waves in the medium into acoustic waves in the carrier in a locally dependent manner, and/or
arranging a material region on a surface of the carrier, which in operation of the device faces the medium, wherein the material region has an acoustic impedance which lies between the acoustic impedance of the medium and the acoustic impedance of the carrier, and/or
arranging a material region which at least partly extends around the transmitter and/or the receiver.

* * * * *